United States Patent [19]

Ferry

[11] Patent Number: 5,767,167
[45] Date of Patent: Jun. 16, 1998

[54] OPEN CELL POLYMERIC FOAM FILTERING MEDIA

[75] Inventor: Laura Lee Ferry, Little Falls, N.J.

[73] Assignee: Petrelli Research, Little Falls, N.J.

[21] Appl. No.: 656,024

[22] Filed: May 31, 1996

[51] Int. Cl.$^6$ ............................................. C08J 9/28
[52] U.S. Cl. ............................................. 521/64; 521/149
[58] Field of Search ................................ 521/64, 149

[56] References Cited

U.S. PATENT DOCUMENTS

| | | | |
|---|---|---|---|
| 3,663,467 | 5/1972 | Albright | 260/2.5 |
| 3,852,388 | 12/1974 | Kimura | 264/41 |
| 4,439,322 | 3/1984 | Sonoda et al. | 210/500.2 |
| 4,818,254 | 4/1989 | Anand et al. | 55/316 |
| 4,873,218 | 10/1989 | Pekala | 502/418 |
| 4,997,804 | 3/1991 | Pekala | 502/418 |
| 5,013,339 | 5/1991 | Mahoney et al. | 55/158 |
| 5,252,620 | 10/1993 | Elliott, Jr. et al. | 521/149 |
| 5,422,377 | 6/1995 | Aubert | 522/64 |
| 5,453,185 | 9/1995 | Frechet et al. | |

OTHER PUBLICATIONS

*Macromolecules* 1986, 19, 1543–1546 Macroporous Gels. 1. Polymerization of Trimethylolpropane Trimethacrylate in Toluene J.E. Rosenberg and P. Flodin.

*Primary Examiner*—Morton Foelak
*Attorney, Agent, or Firm*—Lerner, David, Littenberg, Krumholz & Mentlik

[57] ABSTRACT

Provided are organic aerogel foams and their method of manufacture from polyfunctional vinyl monomers, such as trimethylolpropane trimethacrylate and/or ethoxylated trimethyol trimethacrylate, which foams are ideally suited for filtering media, and especially for microorganism filtration for capture of bacteria, viruses, yeast and other microparticles.

15 Claims, 4 Drawing Sheets

OPEN CELL POLYMERIC FOAM FILTERING MEDIA

FIELD OF THE INVENTION

The present invention relates to polymeric materials which are particularly suited for filtering and/or concentrating media, and more particularly to such organic foams having a continuous pore infrastructure which are manufactured from free radical polymerization of trifunctional or higher functional organic monomers.

BACKGROUND OF THE INVENTION

Many foamed organic polymers and/or otherwise organic foam compositions are known. Representative examples include foams described in U.S. Pat. Nos. 4,694,028; 4,576,972; 4,546,119; 4,525,492; 4,489,175 and 4,417,004. Such foams are generally useful as thermal insulation in the building industry, but are of limited usefulness in applications such as catalysts, in ion exchange reactions, and filter media because of their high discreet cell content, relatively high density and lack of appreciable intra-cell porosity wherein a foam cell framework is interconnected (hereinafter "continuous porosity" or a "continuous pore infrastructure" or otherwise "open cell" structure).

A low density organic foam or aerogel is described in U.S. Pat. Nos. 4,997,804 and 4,873,218 which is said to be useful for high energy physics applications, as parts for inertial confinement fusion targets, and for use in ion exchange reactions. These foams are manufactured from a phenolic substance, such as polyhydroxy benzene, resorcinol, catechol, hydroquinone and various combinations thereof, which undergoes a condensation reaction with formaldehyde in the presence of a base catalyst such a sodium carbonate to form a polymeric gel. The thus formed gel is then exchanged with an organic solvent and supercritically dried with carbon dioxide to produce an aerogel foam said to be of low density and ultra-fine cell size and consisting of a colloidal-like particle matrix with diameters of about 150Å. Other reaction systems said to be suitable for such aerogel formation include 1,3,5- trihydroxybenzene-formaldehyde and melamine-formaldehyde.

Such materials, however, are not useful as filtering media due to the relatively small pore sizes of these foams, which result in poor wetting properties. Further, due to such physical limitations these foams are also not useful as microfiltration devices for bacteria and other microorganisms. Such foams also do not provide a good hydrophilic porous material with a high surface area which can be used for filtration of various gaseous and liquid media.

An important need therefore exists for inert open cell foams which are useful as microfiltration/concentration media, as well as for filtration of various gaseous and liquid media.

SUMMARY OF THE INVENTION

In view of the above, the present invention now provides a low density organic foam of continuous pore infrastructure or otherwise open-cell structure which is ideally suited for filtering medium, and more particularly as a microfiltration or concentration medium. The inventive foam comprises a composition of matter of one or more trifunctional or higher functional organic monomers, such as, for example, trimethylolpropane trimethacrylate and/or ethoxylated trimethylolpropane trimethacrylate, which comprise a interconnected colloidal-like particle matrix forming interconnected pores having an average pore size ranging from less than about 0.1 um to about 2 um.

In another aspect of this invention, there is provided a process for the preparation of such low density organic foams, which comprises mixing one or more trifunctional or higher functional monomers in the presence of a free radical polymerization initiator, under conditions effective to initiate polymerization and gel formation, then drying the gel, either by air drying or critical point drying depending upon the monomer/solvent/initiator system employed and the end results contemplated. The process also may include one more steps of washing the thus formed gel in a suitable organic solvent to exchange the initial organic solvent for an organic solvent having a higher vapor pressure to facilitate the terminal drying step.

The invention is more fully explained by the following detailed description of preferred embodiments with referenced drawings and examples. It is to be understood, however, that the description of preferred embodiments and examples is intended for use as illustrative purposes only, and is not intended to limit the scope of the claims or the spirit of the invention in any way.

DETAILED DESCRIPTION OF PREFERRED EMBODIMENTS

The present invention provides a novel low density foam having a continuous pore infrastructure (a polymeric open cell foam) which is ideally suited for use as filtration medium for the filtration and concentration of micro-matter such as microbes inclusive of bacteria, yeasts, molds, parasites and virus particles, and other micron sized particulate matter and contaminants. The invention also provides foams which are of a hydrophilic porous nature and high surface area, and which are suited for filtration of gaseous and liquid media. The inventive foam filter medium has wide applicability in many industries such as water treatment, environmental applications, food and beverages, clinical and research and development applications, and biotechnological applications.

In a generally preferred approach, the foams of this invention are prepared by a free radical polymerized sol-gel synthetic method in solution. This is accomplished by dilution of a selected trifunctional or higher functional organic monomer or monomer combination in a suitable solvent, such as, for example, acetone, and a free radical initiator, such as benzoyl peroxide, added thereto. The mixture is then heated to catalyze the polymerization of the monomer(s) which form sol particles and which in time link together to form a solid gel. The solvent is then removed from solid polymerized matrix by drying the foam, for example, by air drying or with supercritical drying.

In another preferred approach, depending upon the initial solvent employed, the thus formed solid gel matrix can be washed or otherwise treated so as to exchange the initial solvent with another suitable organic solvent to facilitate foam drying, either by air drying or supercritically.

The trifunctional or higher functional organic monomers employed in this invention are preferably trifunctional or higher functional acrylate-based monomers, some examples of which include trimethyolpropane trimethacrylate (TPT), ethoxylated trimetholypropane triacrylate (TEPT) (or trimethylolpropane ethoxylate), trimethylolpropane propoxylate, pentaerythritol triacrylate and tetraacrylate, glycerol propoxylate triacrylate, tris (2-hydroxyethyl) isocyanurate tri(meth)acrylate, ditrimethylopropane tetraacrylate and pentaacrylate ester. Selected structures of these examples are set forth below.

Trimethylopropane trimethacrylate

Trimethyolpropane triacrylate x = 1, 2 or 3

Trimethylolpropane ethoxylate

Trimethylolpropane propoxylate

Pentaerythritol tetraacrylate

Glycerol propoxylate triacrylate

Tris(2—hydroxyethyl)isocyanorate triacrylate

The use of particular solvents is not critical to the practice of this invention, and can be chosen based on solubility properties for monomers and initiators. Further, after gel formation, solvents may be exchanged by any suitable method such as gel washing for other solvents more suitable for gel drying, such as solvents having a higher vapor pressure.

Particular polymerization initiators are also not critical to the practice of this invention, and can be chosen based on their solubility in a chosen solvent system and their ability to initiate free radical polymerization of monomers in accordance with this invention. For example, several free radical polymerization initiators are known, all of which are effective in a given solvent system to catalyze polymerization of TPT and/or TEPT, and are contemplated for use in this invention. Other illustrative examples include 1,1'-azobis (cyclohexane carbonitrile (DuPont Vazo catalyst 88) and various combinations of sodium metabisulfite and ammonium persulfate.

A typical synthesis of a TPT-based foam is set forth below in example 1, and a TEPT-based foam set forth in Example 2.

EXAMPLE 1

A 0.1g/ml solution of benzoyl peroxide was made up in ethylacetate by adding benzoyl peroxide (0.38/mls) to 2.0 mls ethyl acetate in a 4 ml straight side vial provided with a septum cap. After sparging the contents of the 4 ml vial with nitrogen, separately sparged trimethyolpropane trimethacrylate (TPT) (0.1 mls) was added to the ethyl acetate/benzoyl peroxide solution, and a polymerization reaction is initiated to form a gel by warming the vial in a water bath to approximately 65° C. Polymerization occurred after about one hour, with the vial maintained in the water bath overnight to ensure complete polymerization. A supercritical drying step to remove solvent from the polymerized solid matrix was then carried out by first placing the polymer gel in a beaker of acetone, and exchanging the acetone for ethyl acetate 2–3 times over one to two days, followed by supercritical carbon dioxide extraction of the acetone performed in a pressurized reaction vessel filled with $CO_2$ (or some other suitable gas, for example, nitrogen), above the supercritical point of 800 psi and 35° C. (conditions for a supercritical state of $CO_2$) for approximately 8 hours, after which the pressure was slowly released over about two hours. The end result is a very light, marshmallow-like solid which can be sliced with a razor blade for examination of its surface properties. The surface absorbs water as indicated by its contact angle with water.

EXAMPLE 2

In this experiment, a solution of TPT in acetone (monomer volume to acetone solvent volume 20:80) with free radical initiator 2,2'-azobis-2-methylpropionitrile (AIBN), was prepared with the molar ratio of total monomer to AIBN of 5%. Polymerization was initiated by heating a vial containing the solution to 60° C. in a water bath. After polymerization was complete (overnight), solvent was removed from the foam by supercritical extraction with $CO_2$ performed in a pressurized vessel at >800 psi for approximately 8 hours. After the solvated polymer was equilibrated with supercritical carbon dioxide, the partitioned solvent and $CO_2$ were removed by slowly releasing pressure over two hours, so that the gases can slowly desorb. This foam could absorb water as demonstrated by placing a water droplet on the foam's surface. While not wishing to be limited to any particular theory, such wicking of water into the solid is thought to be due in part to foam structure and pore size, when considering the relatively hydrophobic nature of the TPT monomer. Scanning electron microscopy revealed a microscopic structure wherein sol particles formed by polymerization form a gelled solid.

EXAMPLE 3

Studies of Physical Properties of Foams

Figure 1:
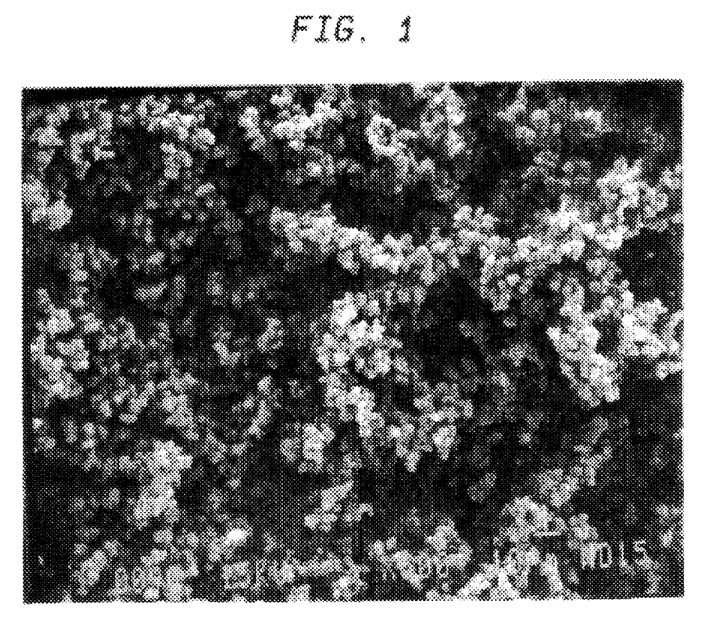
FIGS. 1–3 are micrographs of representative foam structures of the invention.

Further foam examples were manufactured using the a similar procedure as in examples 1 and 2, except that isopropanol was used as the initial solvent, and which was subsequently exchanged with acetone after gel formation and prior to drying. Various proportions of AIBN and benzoyl peroxide initiators are employed with various monomer mixtures of TPT and ethoxylated TEPT. As set forth below in Table 1, a series of polymer foam samples were manufactured with a monomer to solvent ratio of 20% in terms of relative amounts of solvent, monomer and free radical polymerization initiator, and characterization of various physical properties thereof. The proportion of AIBN initiator to monomers was varied from 10% to 0.1% of the number of moles of monomer in three samples examined and examples were also synthesized while varying the relative amounts of TPT and TEPT, for example, by preparing a foam from a solution of TPT:TEPT. The content of the more hydrophobic monomer TPT ranged from 10% to 50% in these samples. A micrograph of a typical foam (75-1, Table 1) with its characteristic structure is shown in FIG. 1..

Again without intending to limit this invention to any particular theory, a study of physical properties of various foams produced in accordance with this invention unexpectedly shows that a relatively smaller proportion of initiator will result in the formation of a foam with smaller sol particles, indicating that gelling occurred before sol particles grew to a large size. This surprising result illustrates a highly desirable feature of the invention with respect to flexibility in foam preparation, such that depending upon the end use contemplated, e.g. pore size and foam morphology v. specific applications, a wide range of foam structures may be easily and conveniently synthesized depending upon the amount of initiator employed.

TABLE 1

Foams Examined for General Properties and Latex Bead Collection by Impaction

| Sample | Monomer: Solvent (% volume of Monomer) | Initiator: Monomer (% of Moles of Initiator) | TPT: TPET (% TPT in Total Monomer) |
|---|---|---|---|
| 75-1 | 20% | 10% | 10% |
| 76-8 | 20% | 10% | 50% |
| 78-7 | 20% | 1% | 50% |
| 81-1 | 20% | 0.1% | 30% |
| 81-3 | 20% | 1% | 30% |
| 81-7 | 20% | 1% | 40% |
| 73-1 | 5% | 2.5% | 50% |

Various physical properties of the presently inventive foams and their performance as microfiltration and/or concentration media have been determined in several studies as set forth below.

POROSITY AND SURFACE AREA

In this study, the magnitude of the surface area and the density of the inventive foams for comparison with other organic and inorganic aerogels and xerogels was undertaken to measure the surface area through the use of a thermal conductivity type surface area instrument, and to also measure the density through the use of helium pycnometry. Foams that were selected the were characterized for their ability to adsorb latex beads.

Surface are measurements were made by physically adsorbing gases onto a solid surface by condensation. Since the pressure dependent interaction between the gas molecules and the surface is through weak Van der Waals forces, the quantity of adsorbed gas will increase with decreasing temperature. Determinations of surface area are typically based upon the analysis of Brunauer, Emmett and Teller (BET analysis), which expanded the dynamic monolayer surface coverage of Langmuir to include more complex capillary and multilayer absorptions. In the thermal conductivity type of surface area analysis, 30% $N_2$ in a helium carrier gas mixture flows through a cell containing the sample. After equilibration with the gases, and the thermal conductivity of the gas is measured. The sample and cell is then cooled to liquid nitrogen temperature by immersion in a dewar, and the thermal conductivity of the gas is monitored. Nitrogen will adsorb onto the surface of the solid, and the decrease in fraction of $N_2$ in the carrier gas mixture is detected by thermal conductivity. The difference in thermal conductivity can be used to determine the amount of $N_2$ removed to adsorption. Warming the sample again results in an equal and negative desorption peak area. The injection of a known amount of 100% $N_2$ gas is used to calibrate the peaks.

Helium pycnometry utilizes the displacement of helium to determine the mass per volume. Helium gas is used to fill an volume $V_0$. The sample is placed in the container, a new $V_1$ is measured, and the difference represents the volume of the material, $V_m$. The weight is determined by the use of an external analytical balance. If closed pores are obtained, the result is an apparent density, while a true density can be obtained if the sample is completely crushed to eliminate closed pores.

Table 2 below describes quantitative results of surface area and measurements. Based upon the formulations described previously, smaller particle sizes associated with higher proportions of initiator result in a foam of higher internal surface area. This can be suggested by a comparison of sample pairs 75-1/76-8 and 81-1/81-3. The density determined by helium pycnometry suggests that the density of the sample is not affected by the morphology of the polymer, since all values of density are similar. However, a crude volume measurement and weight determination with an analytical balance of the density of sample 75-1 (a disc shaped piece 3mm ×12mm diameter) results in a density of 0.062 g/cc. This suggests that the measurements given above are apparent densities instead of true densities of the solid.

TABLE 2

Surface Area and Apparent Density of Foams

| Sample | BET $m^2/g$ | Helium Pycnometry g/cc |
|---|---|---|
| 73-1 | 3.7 | 1.2881 (sd = 0.0336) |
| 75-1 | 21.2 | 1.2785 (sd = 0.0141) |
| 76-8 | 10.7 | 1.2400 (sd = 0.0224) |
| 81-1 | 43.9 | 1.2508 (sd = 0.0022) |
| 81-3 | 36.3 | 1.2462 (sd = 0.0076) |
| 81-7 | 18.3 | 1.3040 (sd = 0.0252) |
| 78-7 | na | na |

COLLECTION OF LATEX BEADS BY IMPACTION

Figure 2:
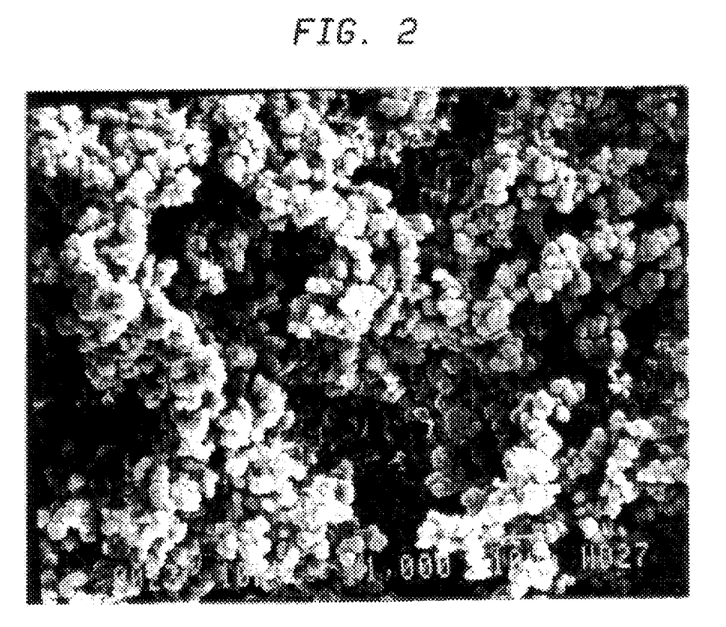
Figure 3:
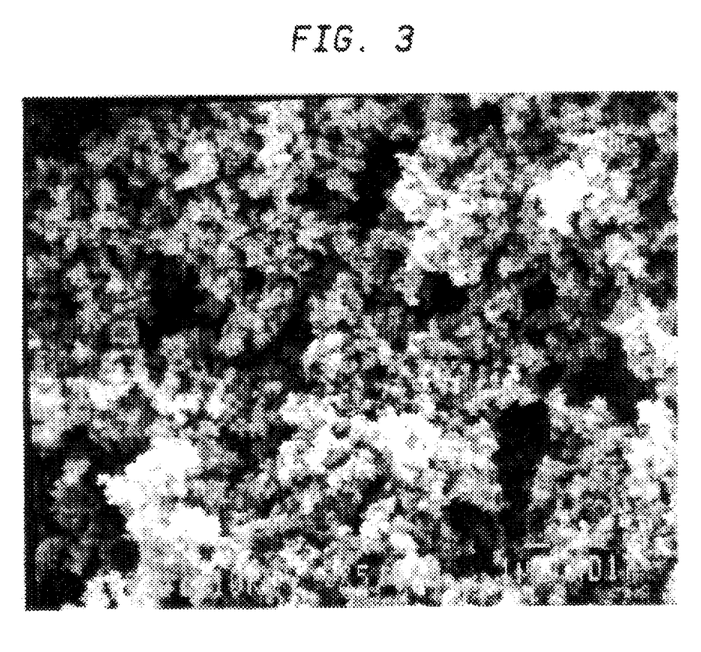

Studies demonstrating latex bead capture by impaction were conducted with foam samples 75-1 (FIG. 1), 76-8 (FIG. 2) and 78-7 (FIG. 3), as described in Table 1, which were prepared to examine their capability of capturing latex beads on the polymeric foam surface to simulate capture of bacteria-sized particles by the presently inventive foams.

Polystyrene beads in distilled water (3 um diameter, Sigma Chemical Co.) were chosen to represent an average diameter of collectable particles. The beads were suspended in distilled water with Tween 20 (Aldrich Chem. Co.) to monodisperse the beads by coating them with the detergent (surfactant). By orienting the surfactant hydrophilic phosphate groups outward, a hydrophilic surface is created which will adhere to the surface of the foam. Examination of the latex beads on an aluminum stub by scanning electron microscopy reveal single and clustered beads, along with a few small vesicles. A membranous film appearing to envelope the beads STET that the Tween 20 has coated the beads.

Disks 1.0 mm thick and 12 mm in diameter were cut from the three foam samples and placed on filter paper. The bead solution was then placed in a pump spray bottle and sprayed in the air over the samples so that the droplets of the surfactant bead composition would eventually drift onto the surface of the polymer foam. These samples were then plasma coated with gold (20–50 um thick) and examined for evidence of the beads. Resulting SEM indicate that samples 75-1 and 76-8 did not capture any latex beads, but sample 78-7 did. Since samples 78-7 and 76-8 have the same monomer composition but different microscopic structure, it is thought that the adsorption of the beads does not occur when the polymer foam sol particles grow to a relatively large size e.g. about 1 um or larger. In the foam samples used, the sol particles comprising the polymer structure are of a size similar to that of the latex beads, and the beads may bounce off the surface of the foam instead of adhering. In contrast, the finer particles of sample 78-7 are very small in comparison to the latex bead, and the bead is therefore able to impact into the surface of the foam and cling to it, assuming, however, that the velocity of the beads is more or less consistent from experiment to experiment during capture and impaction.

Based upon the aforesaid study, a second set of foam samples, 81-1, 81-3 and 81-7 were selected for examination. The second set was placed in an impaction device made of two hollow egg-cup shaped pieces of finished glass, each similar in shape to a glass funnel, with the cup portion of the glass emptying into a glass tube. A foam sample was placed in the center of this formed globe on a disc of filter paper and placed upon a small support. The two halves were sealed to form a glass globe approximately 6 cm in diameter. When sealed, air is able to flow over the surface of the foam, past the paper, and out to a laboratory vacuum line. The air flow was measured by a flowmeter (Dwyer), and maintained at approximately 6 l/min. All three foams were examined with this device by spraying 5 ml of the latex bead solution described above into the air above the device for 2 minutes. The foam samples with adsorbed latex were then coasted with Au/Pd and examined by scanning electron microscopy.

Figure 4:
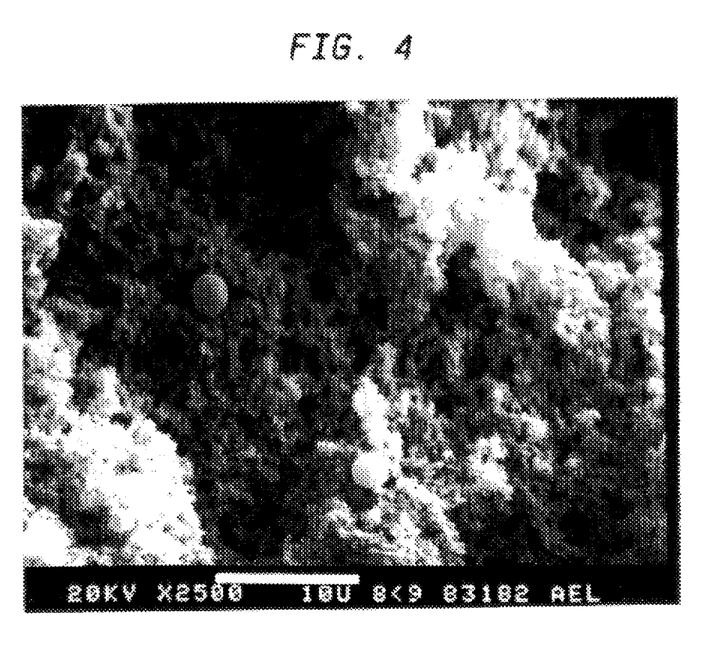
FIGS. 4 and 5 and are sample foams of this invention which have undergone latex bead impaction studies to simulate capture of bacteria-sized particles.
Figure 5:
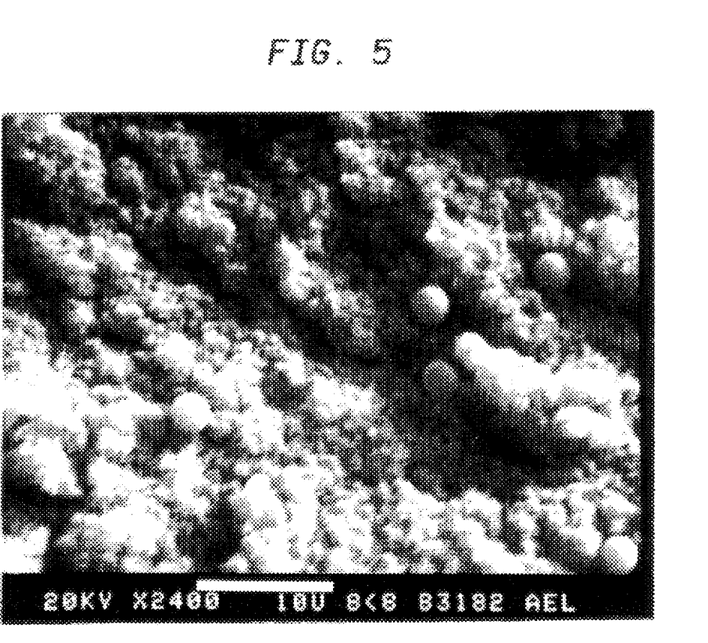
Figure 6:
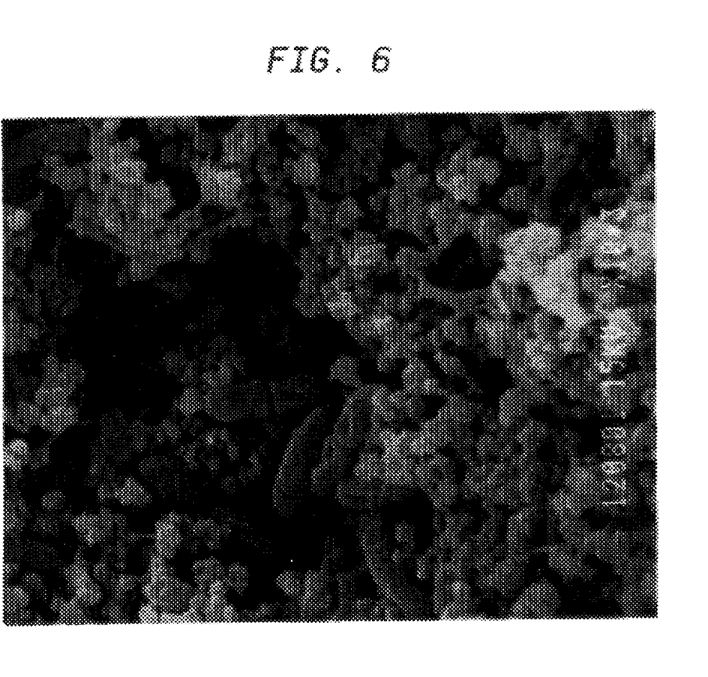
FIGS. 6 and 7 are sample foams of this invention which have been used to collect bacteria.
Figure 7:
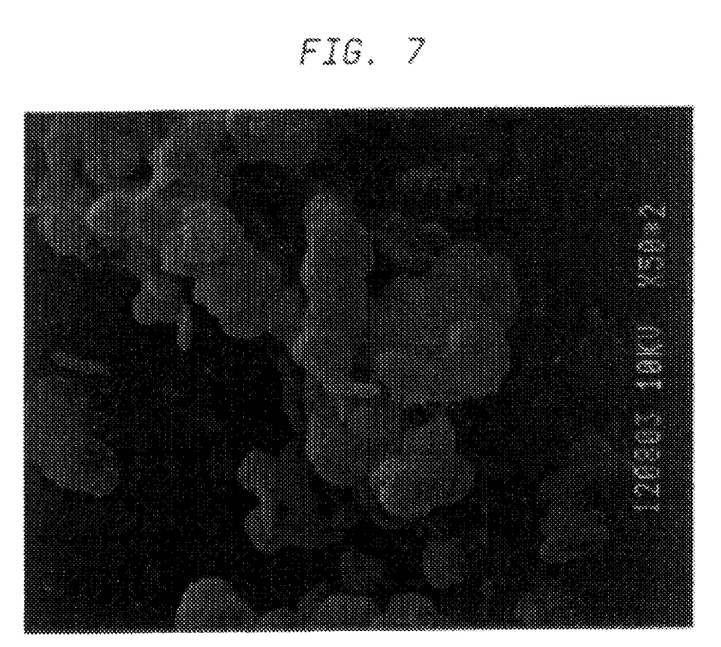

The SEM shows that all three foams were able to collect latex beads as described below in Table 3. See FIG. 4 (Sample 81-3), and FIG. 5 (Sample 81-7) (Sample 81-3 is not shown). The beads were counted over an area of approximately 1637 $um^2$, the amount of area enclosed in a SEM photograph at 2400x. Sample 81-1 collected the greatest density of latex beads, but showed the greatest variation in the number of beads collected per unit area. The density of beads collected decreased in Sample 81-3, but the number of beads collected was more consistent over the surface. Both of these results indicate that a smaller amount of initiator results in smaller sol particles formed before gelling and a greater ability to collect the latex particles.

Sample 81-7 has the same particle size as 81-3, but a greater proportion of TPT monomer. This result suggests that the more hydrophilic sample 81-3 was better able to collect Tween 20 coated latex beads than Sample 81-7. The greater proportion of ethoxylated TPT (TPET) increased the opportunity for dipole-dipole interactions with the beads and increased the ability of the surface to capture the beads.

TABLE 3

Collection of Latex Particles by Foam Impaction

| Sample | Average Number of Particles in 1575 $um^2$ | Range of Number of Particles |
|---|---|---|
| 81-1 | 5–8 | 3–14 |
| 81-3 | 5.75 | 5–7 |
| 81-7 | >1 | 0–2 |

COLLECTION OF LATEX BEADS BY FILTRATION

Air Filtration

The ability of foams manufactured in accordance with this invention to collect aerosolized latex beads by gas filtration was examined as follows. The flow of air through a vacuum line was measured through ¼ inch tygon tubing at 0.9 standard cubic feet/hour. A suspension of latex beads was made as previously described with 0.46 micron diameter latex beads (Sigma LB5) with 0.5% Tween 20 (50 u mls of latex beads in 10 mls of water). Sample 75-2, the composition of which is described in Table 4 below, was utilized in this experiment by placing a 1 mm thick disk of the foam in a 13 mm Gelman filter holder with a Teflon gasket (13 mm plastic swinney filter holder, product #1437-Gelman Sciences). The filter holder was sealed to one end of the tygon tubing with the support screen directed toward the vacuum. The vacuum was turned on and the ambient air was sampled for two minutes at 50% flow while the latex bead solution was aerosolized with a pump spray. The air flow was maintained during the aerosolization of 10 ml of latex bead solution.

The sample of foam was removed from the filter holder, dried in a desiccator overnight, and examined by electron microscopy as previously described. The latex beads were visible on the surface of the foam, and were collected at a density of approximately 4 beads in 25 $um^2$.

Liquid Filtration

The same latex bead solution as described above was utilized to examine the ability of the inventive foams to filter liquid samples. A 1.0 mm thick disk of foam 75-2, (Table 4) was employed in this example, three mls of the liquid latex bead solution were pulled up into a syringe through the polymer foam sample held in the Gelman filter holder. After filtration, the filter holder was removed from the syringe, the foam sample taken out, dried in a desiccator overnight and then examined by electron microscopy as previously described. Latex beads were clearly visible on the foam surface in high density. An approximate count of the density of the beads on this sample was 62 beads per 28 $um^2$.

TABLE 4

Foams Utilized for Collection of Latex Beads and Bacteria by Filtration

| Sample | Monomer: Solvent (% Volume of Monomer) | Initiator: Monomer (% Moles of Initiator) | TPT: TPET (% TPT in Total Monomer) |
|---|---|---|---|
| 71-2 | 20% | 2.5% | 50% |
| 75-2 | 20% | 10% | 20% |
| 75-3 | 20% | 10% | 30% |
| 75-4 | 20% | 10% | 40% |
| 76-1 | 20% | 2.5% | 50% |

COLLECTION OF BACTERIA BY LIQUID FILTRATION

Freeze dried cultures of bacteria were grown to determine the ability of the present inventive foams to capture bacteria by filtration. Three grams of tryptic soy broth (Difco) was placed in 100 mls of water, and sterilized by filtration. A single Bactrol disk of (Difco) *Pseudomonas aeruginosa* was placed in a vial with 1 ml of the sterilized media, dissolved, and left overnight at 37° C. The media and culture became turbid within 18 hours, indicating successful growth of the bacteria. A 5 mM phosphate buffer solution at pH 7 was utilized to dilute 1 ml of the *P. aeruginosa* culture to a total of 5. Foam samples 71-2, 76-1 and 75-3 were utilized to filter the bacteria solutions. Disks of the foam samples that were 1 mm thick and 13 mm across were placed in a Gelman filter holder, and 4 mls were filtered through the disk by filling the barrel of a syringe with the bacterial suspension and ejecting the suspension through the foam in the Gelman filter holder.

The foam samples with bacteria adsorbed to it were then removed from the sample holder for examination by electron microscopy. The samples were then put on a chrome block cooled to −194° C. in liquid nitrogen, and the samples were frozen in liquid propane. They were then put in a freeze dryer for 24 hours to remove all water. After drying, the samples were coated with gold/palladium and examined by electron microscopy. As shown in FIGS. 6 and 7, samples 76-1 and 71-2 respectively, bacteria were collected by the foam by filtration and by sorption.

A second study was carried to examine how solution pH affects the ability of the foam to adsorb bacteria. *E. coli* HB101 (ATCC 33694) was cultured under conditions that were essentially the same as for *P. aerucinosa*. In this experiment, 10 mM biphthalate, phosphate and carbonate buffers at pH 4, 7 and pH 10 were used to make a bacterial suspension of *E. coli*. 4 mls of the suspension at each pH were filtered through disks of foam sample 75-4 by placing the foam in the Gelman holder, as previously described. After filtration of the bacterial suspension through the foam, it was lyophilized and examined by electron microscopy. It was observed that *E. coli* were adsorbed to foam sample 75-4 at pH 4 and 7. At pH 10, few bacteria were visible on the foam.

In a preferred embodiment of the present invention, a filtration/collection apparatus is provided which comprises the inventive foams prepared in situ. As an example, monomer(s), solvent and initiator can be placed in piece of side tubing or other relatively inaccessible structure, and sealed, e.g. with a rubber septum cap. After removal of oxygen by sparging, the monomer containing structure is placed in a heated water to initiate polymerization and to form a gel, after which the initial solvent can be exchanged and the structure then placed in a reaction vessel to remove solvent by critical point drying, to result in an apparatus component with the inventive foam in place and ready for use.

I claim:

1. A method for the preparation of an organic foam comprising the steps of:

a) mixing one or more trifunctional and/or higher functional organic monomers in the presence of a free radical polymerization initiator under conditions effective to initiate polymerization of the monomer or monomers and to form a gel having interconnected pores ranging in size from less than 0.1 microns to about 2 microns;

and b) drying the gel in a pressurized reaction vessel filled with a gas heated under pressure.

2. The method of claim 1, wherein the monomer or monomers are dissolved in a first solvent to which is added a free radical polymerization initiator, and the formed gel is then exchanged in a second solvent having a lower boiling point prior to drying.

3. The method of claim 1 or 2, wherein the monomer is a polyfunctional vinyl monomer.

4. The method of claim 3, wherein the monomer is selected from the group consisting of trimethyolpropane trimethacrylate, (TPT) ethoxylated trimetholypropane tri (meth)acrylate (TEPT), trimethyolpropane triacrylate, ethoxylated trimetholpropane triacrylate, trimethlopropane propoxylate, pentaerythritol tri(meth)acrylate, pentaerythritol tetra(meth)acrylate, glycerol propoxylate tri(meth) acrylate, ditrimethylopropane tetra(meth)acrylate, penta (meth)acrylate ester and tri(2-hydroxyethyl)isocyanurate tri (meth)acrylate.

5. The method of claim 4, wherein the TPT and/or TEPT is in admixture with said free radical initiator in an organic solvent.

6. The method of claim 5, wherein said solvent is isopropanol.

7. The method of claim 5, wherein the ratio of TPT:TEPT ranges from about 10% to about 40%.

8. The method of claim 5, wherein said TPT and/or TEPT comprises about 5% to about 20% of said mixture and said free radical initiator ranges from about 0.1% to about 10% based on the monomer concentration.

9. The method of claim 5, wherein said mixture is heated to a temperature of at least about 65° C.

10. The method of claim 9, wherein said mixture is heated for a time ranging from about 12 to about 24 hours.

11. A method of claim 5, wherein said gas is $CO_2$, and said $CO_2$ is heated under pressure to its critical point.

12. (Amended) A method for manufacture of a filter medium and/or concentration medium comprising the steps of:

a) mixing one or more monomers selected from the group consisting of TPT (trimethylolpropane trimethacrylate) and TEPT (ethoxylated trimethylolpropane triacrylate), wherein said monomer or monomer mixture is present in an amount ranging from about 5% to about 20%, and if both TPT and TEPT are present said TPT:TEPT ratio ranges from about 10% to about 50%, in an organic solvent in the presence of a free radical polymerization initiator present in an amount ranging from about 0.1% to about 10%;

b) heating the mixture for a time and at a temperature effective to form a polymerized gel; and then c) drying the gel in a pressurized reaction vessel filled with a gas heated under pressure to its critical point, which pressure is then slowly released.

13. The method of claim 12, wherein said filter and/or concentration medium has a continuous pore infrastructure with a pore side ranging from about less than 0.1 um to about 2 um.

14. The method of claim 13, wherein said medium is a micro-filter medium.

15. The method of claim 14, whenever said micro-filter medium is suitable for capture of microorganisms selected from the group consisting of bacteria, mold, yeast, parasites, virus particles.

* * * * *